United States Patent [19]
Alexander et al.

[11] 3,958,027
[45] May 18, 1976

[54] EXTRACTION

[75] Inventors: David George Alexander, Kirkella; Allen Forster; David William Farmery, both of Hull, all of England

[73] Assignee: Simon-Rosedowns Limited, England

[22] Filed: June 14, 1974

[21] Appl. No.: 479,493

[52] U.S. Cl. ............................ 426/417; 195/74; 260/112 R; 426/62; 426/429; 426/454
[51] Int. Cl.² ................................................ C12C 11/24
[58] Field of Search ............ 426/454, 417, 468.62, 426/469, 429, 432, 473, 518; 195/28 R, 101, 82, 3, 74, 97, 98; 241/2, 6, 8, 12, 15, 21; 260/112 R

[56] References Cited
UNITED STATES PATENTS

| | | | |
|---|---|---|---|
| 2,172,699 | 9/1939 | Cohn | 426/464 X |
| 2,786,760 | 3/1957 | Bonnafoux | 426/454 |
| 3,441,416 | 4/1969 | Depmer | 426/429 |
| 3,585,179 | 6/1971 | Samejima | 195/28 R X |
| 3,595,749 | 7/1971 | Clark et al. | 195/82 X |
| 3,615,667 | 10/1971 | Joffe | 426/388 X |
| 3,713,838 | 1/1973 | Ziegler | 426/429 X |
| 3,762,930 | 10/1973 | Mahlmann | 426/193 X |

FOREIGN PATENTS OR APPLICATIONS

| | | | |
|---|---|---|---|
| 461,760 | 2/1937 | United Kingdom | 426/518 |

OTHER PUBLICATIONS

*Disintegration of Microorganisms and Preparation of Yeast Cell Walls in a New Type of Disintegrator,* Applied Microbiology, 3/69, pp. 462–466, Article by Rehacek, Beran and Bicik.
*A Study of Grinding Techniques for Bacterial Cells* by Dockstader and Halvorson, in Science, Vol. 112, pp. 618–620.
*Disruption of Mycelia for Enzymes* by K. Zetelaki, found in Process Biochemistry, (British), Dec. 1969, pp. 19–22 and 27.

*Primary Examiner*—Frank W. Lutter
*Assistant Examiner*—N. Greenblum
*Attorney, Agent, or Firm*—Brisebois & Kruger

[57] ABSTRACT

In order to extract oil from yeast powder, the yeast powder is first pelletized, the pellets are flaked, and the resulting flakes are subjected to a solvent extraction process.

3 Claims, No Drawings

EXTRACTION

This invention relates to extraction and is particularly concerned with the solvent extraction of a constituent from natural products of animal or vegetable origin, in powder form. The invention is primarily directed towards extracting oil from yeast powder.

When yeast cells are grown on a substrate of mineral oil, petroleum gas or a waste carbo-hydrate, the product yeast is a mass of unicellular organisms. The yeast when harvested, and after removal of any adherent substrate, is obtained as a fine powder. For extraction of the contained oil, the walls of the yeast cells must be first ruptured, so that, when a solvent for the oil is percolated through the mass of yeast cells, the oil is contacted by the solvent.

However, we have found that yeast powder is so finely divided that proper percolation of a solvent through it is impossible in practice. In an attempt simultaneously to cause cell breakdown and to bring the powder into a form suitable for percolation by a solvent, we have tried to form the powder, in either a cooked or an uncooked state, into flakes by passing the powder through flaking rolls. This expedient however was also unsuccessful, because the yeast powder is so finely divided that either it falls freely through the roll gap of the flaking rolls without compression or, if the feed rate is increased sufficiently, it completely fills the roll gap and the flaking rolls stall.

We have found that the twin aims of rupturing the yeast cell walls and of presenting the yeast powder in a form suitable for subsequent percolation with a solvent are achieved, when the powder is first formed into pellets which are then flaked.

Thus, the present invention resides broadly in a method of extracting a constituent from natural products of animal or vegetable origin, in powder form, the method comprising forming pellets of the powder, flaking the pellets and subjecting the flakes to a solvent extraction process, using a solvent for the required constituent.

As applied to yeast powder, the invention provides a method of extracting oil from yeast powder, the method comprising forming pellets of the yeast powder, flaking the pellets, and subjecting the flakes to a solvent extraction process, by percolating a solvent for the contained oil through the flakes.

Preferably, the yeast powder, prior to pelletizing, is cooked by the application of heat and the addition of steam to bring the moisture content of the powder to about 20% by weight. We have found that a pellet size of approximately one-eighth inch is suitable.

Before extracting the flakes, it is preferred to harden them, by drying the flakes to a moisture content of between 5 and 10% by weight.

The invention will be more readily understood by the following description of an example for extracting oil from yeast powder.

The harvested powder was heated to a temperature between 70° and 80°C in a steam jacketed cooker. At the same time, live steam was allowed into the cooker until the yeast picked up sufficient moisture to have a moisture content of about 20%. The wet powder from the cooker was then fed to a pelleting machine and converted into pellets of approximately ⅛ inch diameter.

The pellets were fed to a pair of flaking rolls by a vibrating feeder, the gap setting of the rolls being chosen to be between 3 and 8 thousandths of an inch. The resulting flakes were well formed, but, being wet, had low mechanical strength. Before further treatment, they were therefore dried in an oven for 40 minutes to reduce the moisture content to between 5 and 10% by weight. The resulting flakes were screened to remove the small amount of fines present, the removed fines being recycled to the pelletiser.

Finally, the flakes were solvent extracted with n-hexane in a continuous solvent extraction device such as that sold under the Registered Trade Mark "ROTO-CEL".

The following Table I shows the importance of rupturing the yeast cells by flaking. In each of the samples of the Table, the yeast after treatment as stated was extracted for 7 hours on a standard Soxhlet extractor. The figures given in the final column represent the oil extracted as a percentage of the original sample less water; the full oil content of the yeast is not easy to determine but is believed to be not in excess of 20% of the water free yeast powder.

TABLE I

| Sample | % Water | % Oil |
| --- | --- | --- |
| Original Powder | 9.0 | 8.6 |
| Powder cooked without moisture addition | — | 7.7 |
| Powder cooked with moisture addition | 21.4 | 9.9 |
| Powder cooked with moisture additon and flaked | 18.9 | 13.3 |
| Powder cooked with moisture addition and pelleted | 20.6 | 14.7 |
| Powder cooked with moisture addition, pelleted and flaked | 19.4 | 18.8 |

It can be seen from this table that even prolonged extraction fails to extract much of the oil from the original powder and vigorous mechanical working is required to give full oil extraction.

While the results in Table I indicate the oil extraction that is obtainable, they do not show whether or not oil extraction is possible in a commercial extraction plant. Table II indicates that that extraction is possible.

TABLE II

| Sample No. | Sample | % Water | Percolation Rate (lbs/hour/sq.ft.) | Solvent Ratio (by weight) | Time Mins. | Residual Oil % |
| --- | --- | --- | --- | --- | --- | --- |
| 1. | Powder cooked with added moisture, pelleted and flaked | 10.9 | 853 | 2.5 : 1 | 90 | 0.6 |
| 2. | Powder cooked with added moisture, pelleted and flaked | | | | | |

TABLE II-continued

| Sample No. | Sample | % Water | Percolation Rate (lbs/hour/sq.ft.) | Solvent Ratio (by weight) | Time Mins. | Residual Oil % |
|---|---|---|---|---|---|---|
|  | then dried | 2.1 | 760 | 2.5 : 1 | 90 | 1.1 |
| 3. | Powder cooked with added moisture, pelleted, flaked and dried, sieved to remove material through 100 mesh (10.8%) | 2.1 | 3,600 | 1.5 : 1 | 60 | 0.9 |
| 4. | Powder cooked with added moisture, pelleted, flaked and dried. Sieve test showed 2.8% through 100 mesh which was not removed | 7.3 | 6,300 | 1.5 : 1 | 60 | 1.0 |

It will be seen that in Sample 1, in which the yeast powder was cooked, pelleted and flaked, good oil recovery was achieved, although a relatively high solvent ratio and a long extraction time was required because the flakes were mechanically weak, as shown by the low percolation rate. Sample 2 demonstrates that no improvement is obtained by strong drying. In Sample 3, 10.8% of fines were removed from the flakes before extraction, resulting in a much improved percolation rate and thus the ability to use a lower solvent ratio and a shorter extraction time. Sample 4 was powder which was cooked with a 20% water addition, pelleted, flaked and then dried to 7.3% moisture (as compared with the 2.1% of Sample 3); the flakes produced were strong and contained only a small quantity of fines and consequently had a very good percolation rate. The figure for residual oil in Sample 4 is closely similar to that of Sample 3, although the drying time was much shorter. The flakes were of a type that could be processed easily in a commercial extractor such as a Rotocel.

What we claim is:

1. A method of extracting oil from a fine yeast powder comprising cells containing said oil, said method comprising the steps of forming pellets of the yeast powder, flaking the pellets in a manner which mechanically ruptures said cells, and subjecting the flakes to a solvent extraction process by percolating a solvent for the contained oil through the flakes.

2. A method according to claim 1, including as a preliminary step, prior to formation of said yeast powder into pellets, the step of treating the powder with steam whereby the moisture content of the powder is increased to about 20% by weight, and wherein the flakes are dried to a moisture content of between 5 and 10% by weight prior to solvent extraction.

3. A method according to claim 1, including as a preliminary step, prior to formation of said yeast powder into pellets, the step of treating the powder with steam at a temperature of between 70° and 80°C whereby the powder is cooked and the moisture content thereof is increased to about 20% by weight, wherein the cooked powder is formed into pellets having a diameter of approximately one-eighth inch and wherein the flakes are dried to a moisture content of between 5 and 10% by weight and are then subjected to solvent extraction with n-hexane.

* * * * *